United States Patent [19]
Jacobs

[11] Patent Number: 5,944,693
[45] Date of Patent: Aug. 31, 1999

[54] SYRINGE ASSEMBLY AND ASSOCIATED SYRINGE BIASING DEVICE

[76] Inventor: Warren A Jacobs, 252A Fulmer Rd., Perkiomenville, Pa. 18074

[21] Appl. No.: 09/135,438

[22] Filed: Aug. 17, 1998

[51] Int. Cl.$^6$ ....................................................... A61M 5/20
[52] U.S. Cl. .............................................................. 604/134
[58] Field of Search .................................. 604/134, 132, 604/135, 207, 208

[56] References Cited

U.S. PATENT DOCUMENTS

| | | | |
|---|---|---|---|
| 126,700 | 5/1872 | Heins . | |
| 2,309,502 | 1/1943 | Douglas . | |
| 4,950,265 | 8/1990 | Taylor | 604/134 |
| 5,239,773 | 8/1993 | Doolittle, Jr. . | |
| 5,318,539 | 6/1994 | O'Neil . | |
| 5,429,607 | 7/1995 | McPhee | 604/134 |
| 5,531,696 | 7/1996 | Menes | 604/208 |
| 5,697,916 | 12/1997 | Schraga | 604/207 |
| 5,722,956 | 3/1998 | Sims et al. | 604/134 |

FOREIGN PATENT DOCUMENTS

| | | | |
|---|---|---|---|
| 579240 | 10/1924 | France | 604/135 |
| 1038718 | 9/1958 | Germany | 604/134 |
| 399187 | 2/1943 | Italy | 604/134 |

*Primary Examiner*—Todd E. Manahan
*Assistant Examiner*—Eduardo C. Robert
*Attorney, Agent, or Firm*—LaMorte & Associates

[57] ABSTRACT

A device for applying a biasing force to a syringe. The syringe is of the type having a barrel, a cannula at one end of the barrel and a piston that extends into the barrel. The biasing device includes a collar element that defines an aperture. The collar element passes over the cannula and abuts against the syringe barrel, wherein the cannula passes through the aperture in the collar element. A cap element is provided that is adapted to engage the piston of the syringe. A plurality of biasing elements extend between the collar element and the cap element. The biasing elements supply a biasing force between the cap element and the collar element that bias the cap element and the collar element toward one another. The biasing force applied between the cap element and the collar element compress the syringe and drive the piston further into the syringe.

13 Claims, 2 Drawing Sheets

SYRINGE ASSEMBLY AND ASSOCIATED SYRINGE BIASING DEVICE

BACKGROUND OF THE INVENTION

1. Field of the Invention

The present invention relates to syringes. More specifically, the present invention relates to syringes that include devices that apply a biasing force to the piston of the syringe and acts to automatically expel material from the syringe.

2. Description of the Prior Art

The prior art record is replete with different types and styles of syringes. Generally, a syringe is a device for dispensing liquid in a controlled manner. Syringes typically contain a barrel and a piston that moves back and forth within the barrel. A cannula communicates with the barrel so that a liquid can be either ejected from, or drawn into, the syringe. If the barrel of a syringe is filled with a liquid and the piston is advanced into the syringe barrel, the liquid will be extruded through the cannula. Conversely, if the syringe barrel is empty and the piston is retracted, a negative pressure will occur within the syringe barrel that will act to draw liquid into the syringe barrel through the cannula.

With a common syringe, a person's hands are used to either advance or retract a piston within a syringe barrel. However, in many applications, it is desired to slowly move the piston of a syringe over a prolonged predetermined period of time. One such application is when a syringe is used to inject an active solution into a tree.

Arborists commonly inject trees with active solutions. The solutions may be antimicrobials, nutritional supplements or herbicides. To inject a tree, the arborist commonly drills a hole into the cambium layer and/or xylem of the tree. A cannula from a syringe is then placed into the drilled hole. The syringe is filled with the active solution. The active solution is slowly ejected from the syringe as the tree absorbs the solution into its sap and distributes the active solution throughout the tree.

It may take a tree hours to absorb all the active solution in a syringe. Obviously, it is not desirable for a person to sit by the syringe for that period of time and apply an extruding bias to the piston of the syringe. For this reason, spring biased syringes have been developed in the prior art. Spring biased syringes contain an integral spring that biases a syringe piston in one direction until all the liquid contained within the syringe barrel is expelled. Such prior art syringes are exemplified by U.S. Pat. No. 5,239,773 to Doolittle, entitled Tree Injection System; U.S. Pat. No. 5,318,539 to O'Neil, entitled Liquid Feeding Apparatus Utilizing Capillary Tubing And Syringe Driver; and U.S. Pat. No. 5,693,021 to Diaz, entitled Catheter Exchange Device.

With all the spring biased syringes cited, the syringes are custom manufactured with the spring being an integral part of the syringe's design. Such spring biasing mechanisms cannot therefore be retroactively added to common syringes. Since the spring bias mechanism of such prior art syringes are integrally designed as part of the syringes, the springs of the syringe automatically become compressed when the syringe is filled. Since the syringes are commonly filled with active ingredients that many be harmful to humans, the syringes have the potential of expelling that harmful material if accidently activated. According, filled prior art syringes are dangerous to transport and handle. A need therefore exists for a system where a spring biasing mechanism can be selectively added to common inexpensive syringes after the syringe is safely applied. The syringe can therefore be safely transported and handled without the contents of the syringe being under pressure. After being used, the spring biasing mechanism can be removed and the syringe can be either refilled or disposed. The spring biasing mechanism can then be used again on the same syringe or on another syringe.

SUMMARY OF THE INVENTION

The present invention is a device for applying a biasing force to a syringe. The syringe is of the type having a barrel, a cannula at one end of the barrel and a piston that extends into the barrel. The biasing device includes a collar element that defines an aperture. The collar element passes over the cannula and abuts against the syringe barrel, wherein the cannula passes through the aperture in the collar element. A cap element is provided that is adapted to engage the piston of the syringe. A plurality of biasing elements extend between the collar element and the cap element. The biasing elements supply a biasing force between the cap element and the collar element that bias the cap element and the collar element toward one another. The biasing force applied between the cap element and the collar element compress the syringe and drive the piston further into the syringe.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE INVENTION

Although the present invention assembly can be used in many different applications, the present invention assembly is particularly useful in slowly injecting an active solution into the xylem layer of a tree over a prolonged period of time. As a result, the present invention assembly will be primarily described in an application for injecting trees in order to set forth the best mode contemplated for the device.

Figure 1:
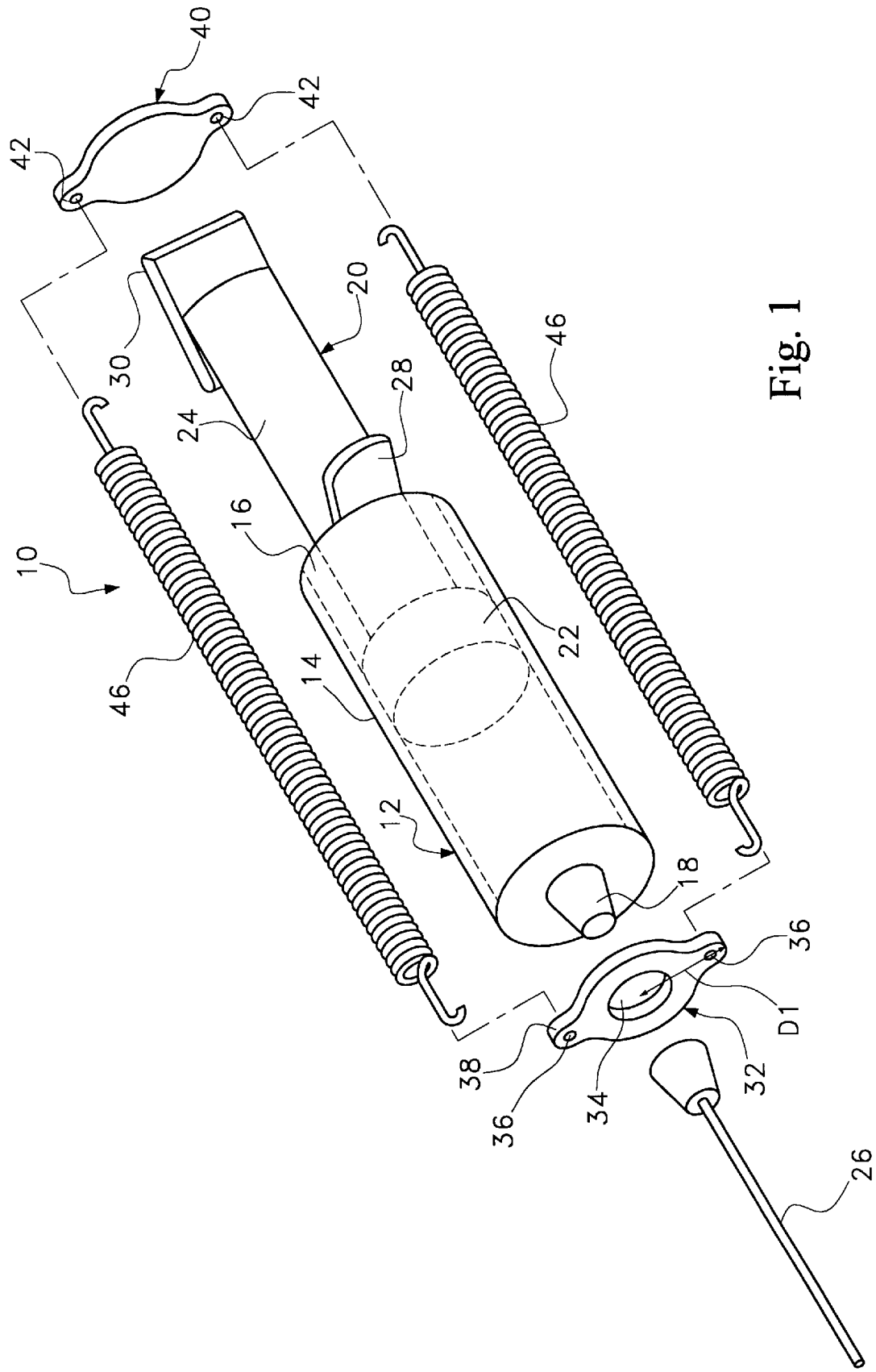
FIG. 1 is an exploded perspective view of an exemplary embodiment of a syringe assembly in accordance with the present invention.

Referring to FIG. 1, an exemplary embodiment of the present invention assembly 10 is shown. The assembly 10 contains a typical prior art syringe 12. The syringe 12 contains a barrel 14 having an open distal end 16 and a narrow open neck 18 at its proximal end. The syringe 12 also contains a piston assembly 20 that works in unison with the syringe barrel 14. The piston assembly 20 contains a piston head 22 disposed at the end of a piston shaft 24. The piston head 22 enters the open distal end 16 of the syringe barrel 14 and creates a fluid impervious seal against the interior of the syringe barrel 12. The piston head 22 is advanced into the syringe barrel 14 by the piston shaft 24. As the piston head 22 advances, the piston head 22 extrudes any liquid contained within the syringe barrel 14 through the open neck 18 of the syringe barrel 14.

The neck 18 of the syringe barrel 14 is adapted to receive a hollow needle or some other form of cannula 26. The exterior of the syringe neck 18 can be threaded to accept the cannula 26 or can be sized to engage the cannula 26 with an interference fit.

The syringe 12 also contains radially extending finger flanges 28 that extend from the syringe barrel 14 proximate the open distal end 16. The finger flanges 28 assist a person to engage the syringe barrel 14 with his/her fingers when manually manipulating the syringe 12. Similarly, an end flange 30 is disposed that the end of the piston shaft 24. The end flange 30 enables a person to comfortably press against the piston shaft 30 when the piston shaft 30 is manually advanced into the syringe barrel 14.

In FIG. 1, a biasing mechanism in accordance with the present invention is also shown. The biasing mechanism included a collar element 32 that engages the proximal end of the syringe barrel 14. The collar element 32 defines a central aperture 34. The central aperture 34 is sized to be larger than the neck 18 of the syringe barrel 14 yet smaller than the main body of the syringe barrel 14. Accordingly, the collar element 32 can be slipped over the neck of the syringe barrel 14 by passing the neck 18 of the syringe barrel 14 into the central aperture 34.

At least two attachment structures 36 are disposed proximate the periphery of the collar element 32. In the shown embodiment, the attachment structures 36 are small apertures. However, it should be understood that other attachment structures such as hooks, hoops and the like could also be used. Also in the shown embodiment, the attachment structures 36 are disposed in tabs 38 that radially extend from the collar element 32. Such tabs are optional. The attachment structures 36 can be attached to any part of the collar element 32 provided that the distance D1 from the center of the aperture 34 to the attachment structure 36 is greater than the radius of the main body of the syringe barrel 14.

A cap element 40 is also provided. The cap element 40 abuts against the end flange 30 of the piston shaft 24, as will later be explained. The cap element 40 also contains attachment structures 42. The location and number of attachment structures 42 on the cap element 40 correspond to the location and number of attachment structures 36 on the collar element 32. Accordingly, the attachment structures 36, 42 on the collar element 32 and the cap element 40 align in parallel lines. The attachment structures 36, 42 on both the collar element 32 and the cap element 40 are positioned so that they do not interfere with the location of the finger flanges 28 extending radially from the distal end 16 of the syringe barrel 14.

Bias elements 46 are attached to the attachment structures 36 on the collar element 32 and the attachment structures 42 on the cap element 40. In the shown embodiment, the bias elements 46 are springs. However, it should be understood that elastic elements can be used in place of springs, if desired. The bias elements 46 act to bias the collar element 32 and the cap element 40 toward one another. The force of the bias is determined by the physical characteristics of the bias elements 46 used. For example, if springs are used as the bias elements 46, the bias applied by the springs can be controlled by changing the length and spring constant of the springs.

To utilize the present invention assembly, an active solution is drawn into the syringe barrel 14 using traditional techniques. Once the syringe barrel 14 is filled with the desired volume of active solution, the syringe 12 is placed within the biasing mechanism. The cannula 26 at the tip of the syringe 12 is passed through the aperture 34 in the center of the collar element 32. The syringe barrel neck 18 is also advanced through the aperture 34 until the collar element 32 abuts against the main body of the syringe barrel 14.

The cannula 26 of the syringe 12 is then applied to its desired application. In the present example, the cannula is inserted into a hole in a tree (not shown). Once applied, the biasing mechanism is fully engaged with the syringe. To engage the syringe 12 with the biasing mechanism, the cap element 40 is manually pulled away from the collar element 32 and placed over the end flange 30 at the end of the piston shaft 24. As the cap element 40 is placed over the end flange 30 of the piston shaft 24, the bias elements 46 are elongated. Consequently, the bias elements 46 provide a contracting force that acts to bias the extended cap element 40 back toward the collar element 32. The contacting force is transferred to the piston shaft 24 as the cap element 40 is brought into abutment with the end flange 30 at the end of the piston shaft 24.

The compression force applied by the bias elements 46 causes the piston shaft 24 to advance into the syringe barrel 14. This has the effect of extruding the active solution out of the syringe barrel 14 through the cannula 26. The compression force applied by the biasing elements 46 is continuous until either the piston head 22 hits bottom in the syringe barrel 14 or the bias elements 46 contract to their nominal lengths.

Figure 2:
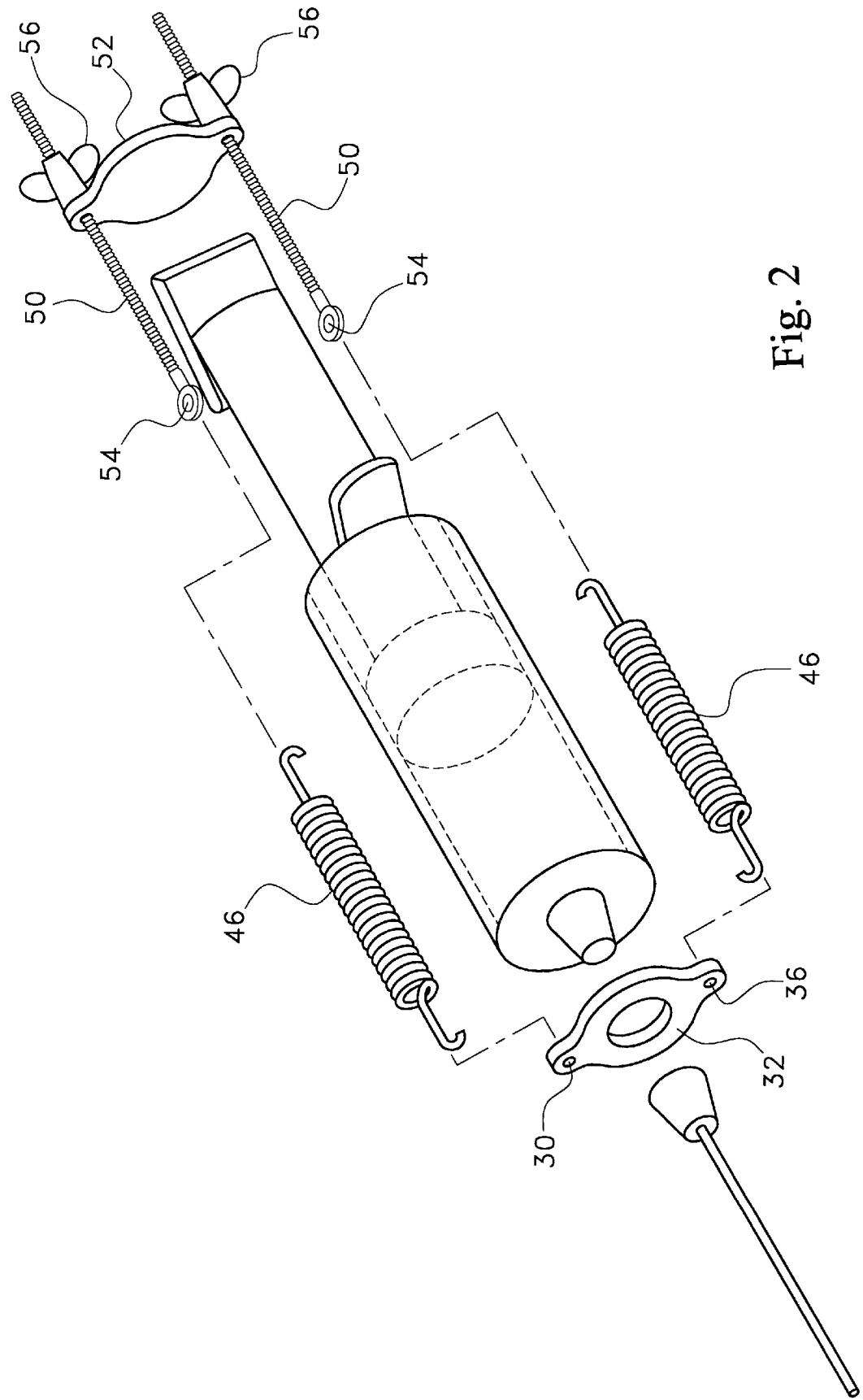
FIG. 2 is an exploded perspective view of an alternate embodiment of a syringe assembly in accordance with the present invention.

Referring to FIG. 2, an alternated embodiment of a biasing mechanism is shown. The alternate embodiment shares many of the same features as the exemplary embodiment of FIG. 1. As such, similar features are referenced with the same reference numerals as were used in FIG. 1. In FIG. 2, two screws 50 extend through cap element 52. Attachment structures 54 are disposed at the head of the screws 50. A wing nut 56 or similar fastener engages each screw 50 as it passes through the cap element 52. The biasing elements 46 attach to the head of the screw 50 and the attachment structures 36 on the collar element 32. The length of the screws 50 below the cap element 52 can be selectively varied by adjusting the wing nuts 56 along the length of the screws 50. The longer the screws 50 extend below the cap element 52, the lesser the bias elements 46 must stretch. The lesser the stretch of the biasing elements 46, the lesser the force that is applied by the biasing elements 46. Consequently, by adjusting the length of the screws 50, the force applied by the biasing elements 46 can be selectively controlled to fit the needs of the user.

In the embodiments of FIG. 1 and FIG. 2, the shown biasing elements were coil springs with a constant diameter. With such springs, the force applied by the springs is directly proportional to the degree by which the springs are stretched. It should be understood that different types of springs can be used. For example, the biasing elements can be conically shaped coil springs. Conically shaped coil springs can be designed to apply a constant biasing force throughout a large range of deformations. Consequently, the force applied to a syringe plunger can be maintained near a constant while under the influence of the syringe biasing device.

It will be understood that the embodiments of the present invention described and illustrated herein are merely exemplary and a person skilled in the art can make many variations to the embodiment shown without departing from the scope of the present invention. There are many different devices that can be used as biasing elements. Furthermore, there are many different shapes into which the collar element and the cap element can be formed. All such variations, modifications and alternate embodiments are intended to be included within the scope of the present invention as defined by the appended claims.

What is claimed is:

1. An assembly, comprising:

a syringe barrel having a narrow opening at one end and a large opening at an opposite end;

a piston shaft having a first end and a second end, wherein said first end of said piston shaft extends into large opening of said syringe barrel;

a piston head coupled to said first end of said piston shaft, wherein said piston head creates a fluid imperious seal within said syringe barrel;

a collar element contacting said syringe barrel wherein said collar element defines an aperture and said narrow opening of said syringe barrel is oriented within said aperture;

a cap element contacting said second end of said piston shaft;

screws extending a predetermined distance from said cap element toward said collar element; and at least one biasing element extending between said collar element and said screws, wherein said at least one biasing element applies a biasing force to said cap element, through said screws, that causes said cap element to bias said piston shaft into said syringe barrel.

2. The assembly according to claim 1, wherein said at least one biasing element is a spring.

3. The assembly according to claim 1, wherein said at least one biasing element is configured to include a plurality of biasing elements.

4. The assembly according to claim 1, further including a cannula that attaches to said syringe barrel at said narrow opening.

5. The assembly according to claim 1, further including a mechanism for adjusting said biasing force applied by at least one biasing element.

6. The assembly according to claim 1, further including a mechanism for selectively adjusting said predetermined distance.

7. A device for applying a biasing force to a syringe of the type having a barrel, a cannula at one end of the barrel and a piston that extends into the barrel, said device comprising, a collar element that defines an aperture;

a cap element;

screw elements that engage said cap element and extend from said cap element toward said collar element, wherein said screw elements extend a first distance toward said collar element; and a plurality of biasing elements extending between said collar element and said screw elements that supply a biasing force between said cap element and said collar element, thereby biasing said cap element and said collar element toward one another once separated by a predetermined distance.

8. The device according to claim 7, wherein said plurality of biasing elements are springs.

9. The device according to claim 7, further including a mechanism for adjusting said biasing force applied by said biasing elements.

10. The device according to claim 7, further including a mechanism for selectively adjusting said first distance that said screw elements extend from said cap element.

11. The device according to claim 7, wherein said collar element contains flanges that radially extend from said collar element, wherein said biasing elements attach to said flanges.

12. A method of applying a biasing force to a syringe, wherein the syringe includes a barrel, a cannula coupled to the barrel and a piston shaft extending into the barrel, said method comprising the steps of:

placing a collar element around syringe wherein said cannula element passes through said collar element and said collar element abuts against the syringe barrel;

advancing screws through said collar element, so that said screws extend a predetermined distance from said collar element; placing a cap element in abutment with the piston shaft;

biasing said cap element toward said collar element by positioning a plurality of biasing elements between said cap element and screws that extend from said collar element.

13. The method according to claim 12 further including the step of adjusting the biasing force applied by said biasing elements by varying the predetermined distance said screws extend from said collar element.

* * * * *